United States Patent
Nguyen et al.

(10) Patent No.: US 11,701,036 B2
(45) Date of Patent: Jul. 18, 2023

(54) SALIVA TEST STRIP AND METHOD

(71) Applicant: MX3 Diagnostics, Inc., Austin, TX (US)

(72) Inventors: Thanh Cong Nguyen, Sunshine West (AU); Efstratios Skafidas, Thornbury (AU); Duc Hau Huynh, Lalor (AU); Michael Erlichster, Caulfield North (AU); Duc Phuong Nguyen, Deer Park (AU); Hsien Ming, Footscray (AU); Gursharan Chana, Fitroy North (AU); Ting Ting Lee, Footscray (AU); Chathurika Darshani Abeyrathne, Mitcham (AU); You Liang, Carlton (AU); Trevor John Kilpatrick, Parkville (AU); Michael Luther, Austin, TX (US); Alan Dayvault Luther, Edina, MN (US)

(73) Assignee: MX3 Diagnostics, Inc., Austin, TX (US)

( * ) Notice: Subject to any disclaimer, the term of this patent is extended or adjusted under 35 U.S.C. 154(b) by 381 days.

(21) Appl. No.: 16/924,386

(22) Filed: Jul. 9, 2020

(65) Prior Publication Data
US 2021/0007646 A1    Jan. 14, 2021

Related U.S. Application Data

(60) Provisional application No. 62/872,339, filed on Jul. 10, 2019.

(51) Int. Cl.
*A61B 5/145* (2006.01)
*A61B 10/00* (2006.01)
(Continued)

(52) U.S. Cl.
CPC ...... *A61B 5/14546* (2013.01); *A61B 10/0051* (2013.01); *B01L 3/502715* (2013.01);
(Continued)

(58) Field of Classification Search
CPC ........... A61B 5/14546; A61B 10/0051; A61B 2562/0295; A61B 5/4875; A61B 5/14507;
(Continued)

(56) References Cited

U.S. PATENT DOCUMENTS 4,454,007 A    6/1984  Pace
5,714,341 A    2/1998  Thieme et al.
(Continued)

FOREIGN PATENT DOCUMENTS

CN    109682878 A  *  4/2019  ............ B01L 3/5025
EP    1710565 A1    10/2006
(Continued)

OTHER PUBLICATIONS

"Cepheid and Sherlock Biosciences Establish Collaboration on New GeneXpert Tests for Infectious Diseases and Oncology Leveraging CRISPR Technology, http://cepheid.mediaroom.com/2020-02-28-Cepheid-and-Sherlock-Biosciences-Establish-Collaboration-on-New-GeneXpert-Tests-for-Infectious-Diseases-and-Oncology-Leveraging-CRISPR-Technology, 3 pages (Feb. 28, 2020).".
(Continued)

*Primary Examiner* — Dennis White
(74) *Attorney, Agent, or Firm* — Knobbe, Martens, Olson & Bear LLP

(57) ABSTRACT

A test strip for sampling a bodily fluid may include multiple layers of a substrate material, an adhesive between at least some of the multiple layers, and a microfluidic channel formed between at least some of the multiple layers. The test strip may further include multiple electrodes on one of the multiple layers, positioned and partially exposed within the
(Continued)

microfluidic channel, an additional material positioned at or near an entrance to the microfluidic channel, to selectively limit the flow of at least one of bubbles or debris into the microfluidic channel, and at least one exit port in at least one of the multiple layers to allow for release of pressure from the test strip. In some embodiments, the test strip is a saliva analysis test strip. In some embodiments, the test strip includes multiple exit ports to prevent blockage of sample flow.

21 Claims, 13 Drawing Sheets

(51) Int. Cl.
 *B01L 3/00* (2006.01)
 *G01N 27/327* (2006.01)
(52) U.S. Cl.
 CPC ......... *B01L 3/502723* (2013.01); *B01L 3/567* (2013.01); *G01N 27/3272* (2013.01); *A61B 2562/0295* (2013.01); *B01L 2300/123* (2013.01); *B01L 2400/06* (2013.01)
(58) Field of Classification Search
 CPC .............. A61B 5/4277; B01L 3/502715; B01L 3/502723; B01L 3/567; B01L 2300/123; B01L 2400/06; B01L 2200/0631; B01L 2200/0684; B01L 2300/0645; B01L 2300/069; B01L 2300/0825; B01L 2300/126; B01L 3/5023; G01N 27/3272
 See application file for complete search history.

(56) References Cited

U.S. PATENT DOCUMENTS

| | | | |
|---|---|---|---|
| 6,086,748 A | 7/2000 | Durst et al. | |
| 6,102,872 A | 8/2000 | Doneen et al. | |
| 6,554,982 B1 | 4/2003 | Shin et al. | |
| 9,546,973 B2 | 1/2017 | Mcilrath | |
| 10,197,523 B2 | 2/2019 | Huang et al. | |
| 10,258,278 B2 | 4/2019 | Howell et al. | |
| 10,989,724 B1 | 4/2021 | Holmes et al. | |
| 2001/0032785 A1 | 10/2001 | Cha et al. | |
| 2002/0011408 A1 | 1/2002 | Lee et al. | |
| 2002/0060247 A1 | 5/2002 | Krishnaswamy et al. | |
| 2002/0065332 A1 | 5/2002 | Choi et al. | |
| 2003/0150745 A1 | 8/2003 | Teodorczyk et al. | |
| 2003/0171697 A1 | 9/2003 | Smith et al. | |
| 2004/0238358 A1* | 12/2004 | Forrow .............. | C12Q 1/001 204/403.01 |
| 2005/0143675 A1* | 6/2005 | Neel ................. | A61B 5/15117 600/583 |
| 2005/0279647 A1 | 12/2005 | Beaty | |
| 2006/0137980 A1 | 6/2006 | Lauks et al. | |
| 2007/0015287 A1 | 1/2007 | Robbins et al. | |
| 2007/0048224 A1 | 3/2007 | Howell et al. | |
| 2007/0073127 A1 | 3/2007 | Kiani et al. | |
| 2007/0098600 A1* | 5/2007 | Kayyem .......... | B01L 3/502738 435/293.1 |
| 2007/0272564 A1 | 11/2007 | Huang | |
| 2008/0118397 A1 | 5/2008 | Slowey et al. | |
| 2009/0024060 A1 | 1/2009 | Darrigrand et al. | |
| 2009/0173629 A1 | 7/2009 | Kidwell | |
| 2010/0176006 A1 | 7/2010 | Bickford et al. | |
| 2010/0249652 A1 | 9/2010 | Rush et al. | |
| 2011/0162978 A1 | 7/2011 | Cardosi et al. | |
| 2012/0067741 A1 | 3/2012 | Kranendonk et al. | |
| 2012/0083711 A1 | 4/2012 | Goldstein et al. | |
| 2012/0109011 A1 | 5/2012 | Cogan et al. | |
| 2012/0165626 A1 | 6/2012 | Irina et al. | |
| 2012/0282616 A1 | 11/2012 | Zeijlstra et al. | |
| 2012/0289863 A1 | 11/2012 | Goldstein et al. | |
| 2013/0199944 A1 | 8/2013 | Petisee | |
| 2013/0233061 A1 | 9/2013 | Sullivan | |
| 2013/0341186 A1* | 12/2013 | Hsu ................. | G01N 27/3272 204/403.14 |
| 2014/0277291 A1 | 9/2014 | Pugh et al. | |
| 2014/0326037 A1 | 11/2014 | Fukuda et al. | |
| 2015/0091592 A1 | 4/2015 | Elder | |
| 2015/0216471 A1 | 8/2015 | Goldstein et al. | |
| 2015/0217115 A1 | 8/2015 | Avitall | |
| 2015/0226695 A1 | 8/2015 | Bakker et al. | |
| 2015/0226752 A1 | 8/2015 | Nazareth et al. | |
| 2015/0359458 A1 | 12/2015 | Erickson et al. | |
| 2016/0011178 A1 | 1/2016 | Hoenes et al. | |
| 2016/0120468 A1 | 5/2016 | Mathew et al. | |
| 2016/0266102 A1* | 9/2016 | Knopfmacher .. | G01N 33/48792 |
| 2016/0320326 A1 | 11/2016 | Zevenbergen et al. | |
| 2016/0361001 A1 | 12/2016 | Tai et al. | |
| 2017/0014822 A1 | 1/2017 | Ker | |
| 2017/0027506 A1 | 2/2017 | Howell et al. | |
| 2017/0067889 A1 | 3/2017 | Tamir | |
| 2017/0138962 A1 | 5/2017 | Southern | |
| 2017/0261461 A1 | 9/2017 | Bychkova et al. | |
| 2018/0125400 A1 | 5/2018 | Yang et al. | |
| 2018/0220947 A1 | 8/2018 | Bedell, Jr. | |
| 2019/0150836 A1 | 5/2019 | Skafidas et al. | |
| 2020/0011851 A1 | 1/2020 | Piasio et al. | |
| 2020/0116664 A1 | 4/2020 | Abeyrathne et al. | |
| 2020/0383582 A1 | 12/2020 | Bychkov | |
| 2021/0005233 A1 | 1/2021 | Kim et al. | |
| 2021/0005322 A1 | 1/2021 | Huynh et al. | |
| 2021/0215662 A1 | 7/2021 | Erlichster et al. | |
| 2021/0223239 A1 | 7/2021 | De et al. | |
| 2021/0239586 A1 | 8/2021 | Skafidas et al. | |
| 2022/0013212 A1 | 1/2022 | Tseng et al. | |
| 2022/0122743 A1 | 4/2022 | Erlichster et al. | |
| 2022/0143609 A1* | 5/2022 | Xu ................. | B01L 3/502723 |

FOREIGN PATENT DOCUMENTS

| | | |
|---|---|---|
| EP | 2075339 A1 | 7/2009 |
| KR | 20160035584 A | 3/2016 |
| WO | WO2010045247 A1 | 4/2010 |
| WO | WO2011075711 A1 | 6/2011 |
| WO | 2014176753 A1 | 11/2014 |

OTHER PUBLICATIONS

"Cepheid, Xpert Carba-R, GXCARBAR-10, https://www.cepheid.eom/Package%20Insert20Files/Xpert-Carba-R-RX-Only-US-IVD-ENGLISH-Package-Insert-301-2438-Rev-F.pdf, Rev. F, 54 pages (Aug. 2019).".

Erlichster et al., "Assessment of Biomarker Concentration in a Fluid," U.S. Appl. No. 62/961,438, filed Jan. 15, 2020, 22 pages.

Erlichster et al., "Pan-Family Assays for Rapid Viral Screening: Reducing Delays in Public Health Responses During Pandemics", Clinical Infectious Diseases, Jul. 20, 2020 (Jul. 20, 2020), pp. 1-6, XP055830068.

Erlichster et al., "Personalized Hydration Assessment and Fluid Replenishment," U.S. Appl. No. 62/876,263, filed Jul. 19, 2019, 30 pages.

Erlichster et al., "Personalized Hydration Assessment and Fluid Replenishment," U.S. Appl. No. 62/957,527, filed Jan. 6, 2020, 35 pages.

Nguyen et al., "Saliva Test Strip and Method" U.S. Appl. No. 62/872,339, filed Jul. 10, 2019, 31 pages.

Paul K et al., "The arrival of a true point-of-care molecular assay-ready for global implementation?", Nov. 1, 2015 (Nov. 1, 2015), pp. e663-e664, XP055830065.

Skafidas et al., "Biological Fluid Sample Assessment," U.S. Appl. No. 62/967,694, filed Jan. 30, 2020, 21 pages.

Oncescu et al., "Smartphone based health accessory for colorimetric detection of biomarkers in sweat and saliva," Lab on a Chip 13(16):3232-3238, Jun. 7, 2013.

(56) References Cited

OTHER PUBLICATIONS

A. Moya, et al., "Flexible Microfluidic Bio-Lab-on-a-Chip Multi-Sensor Platform for Electrochemical Measurements", Sensors, 2014 IEEE, pp. 1018-1021 (Year: 2014).

* cited by examiner

SALIVA TEST STRIP AND METHOD

CROSS REFERENCE TO RELATED APPLICATIONS

This application claims priority to U.S. Provisional Patent Application Ser. No. 62/872,339, titled "Saliva Test Strip and Method," filed Jul. 10, 2019, the full disclosure of which is hereby incorporated by reference herein.

TECHNICAL FIELD

This application describes biomedical systems and methods. More specifically, the application describes a test strip and accompanying system and method for analyzing saliva and/or other bodily fluids to measure one or more physiological parameters.

BACKGROUND

Appropriate hydration in the human body is vital for health and proper functioning of the body organs. Water is lost from the body during respiration, perspiration and urination. Fluid loss of just a few percent can negatively impact cardiovascular function, thermal dissipation, and exercise performance. Dehydration can cause headaches, light-headedness, dizziness, fainting and in extreme cases delirium, unconsciousness or even death. Hyponatremia ("over-hydration") can also detrimentally affect the body's functioning, particularly during exercising, and can even lead to death in extreme cases.

Dehydration is an excessive loss of body fluid. In physiological terms, dehydration may entail a deficiency of fluid within an organism. Dehydration can be caused by losing too much fluid, not drinking enough fluids, or both. Vomiting, diarrhea, and excessive perspiration without sufficient liquid intake are other causes of dehydration, which may be particularly worrisome for athletes and people that work under hot, dry conditions. There are three main types of dehydration: hypotonic (primarily a loss of electrolytes, especially sodium), hypertonic (primarily a loss of water), and isotonic (equal loss of water and electrolytes). While isotonic dehydration is the most common, distinction between the three types of dehydration may be important for administering proper treatment.

Relying on thirst as a feedback mechanism to trigger demand for fluid intake may not be adequate to maintain an optimal hydration level, since a sensation of thirst sufficient to cause a subject to drink is often not triggered until after the subject is already dehydrated. Unfortunately, there are currently no practical, affordable, non-invasive devices for measuring a person's hydration level. Measurement devices that use blood or urine to measure hydration are impractical, invasive, and/or prohibitively expensive.

Many other physiological parameters and levels of various substances in the human or animal body are frequently tested or would be desirable to test for. Unfortunately, it is often necessary to sample blood, urine or other bodily substances, such as cerebrospinal fluid, to measure a desired parameter. Some physiological parameters involve even more invasive or costly measurement techniques.

Therefore, it would be highly beneficial to have a practical, affordable, non-invasive system and method for measuring a person's hydration level. It would also be very desirable to have practical, affordable, non-invasive systems and methods for testing other parameters in the body.

Saliva is a rich source of biomarkers, which can be used to monitor health and wellness, including hormones, metabolites, nucleic acids and drugs. One challenge of analyzing saliva is that it can have markedly varying properties. Saliva also exhibits non-Newtonian dynamics, where the reaction force increases disproportionally with the amount of force applied. Furthermore, saliva is prone to contamination from food, salts, liquids, debris, cells and bacteria. The viscosity of saliva can vary significantly from person to person and even for the same person, based on temperature, mucus content, age, diet and health status. Mucus, in particular, can transport contamination and cause bubbles to form in saliva. Debris and bubbles significantly confound the reliability of electrochemical (e.g., amperiometric, voltametric, impediometric) and optical techniques used to measure ions, molecules, cells and other compounds in saliva. Additionally, collection of saliva can by complicated by mouth dryness or hyper-salivation Due to these challenges, existing saliva-based tests typically require collection with specific collection apparatus and sample processing prior to analysis.

Therefore, it would be desirable to develop an improved test strip for saliva collection. Ideally, such a test strip would provide for consistent sample collection directly from the mouth or simple collection receptacle without additional processing. Also ideally, the test strip would help prevent or remove contaminants and bubbles. Additionally, it would be ideal to have a test strip that could consistently collect a sample by directly contacting the strip with the subject's tongue, thus allowing for sampling without clear visibility of the sample source. This application addresses at least some of these objectives.

SUMMARY

Saliva may be an ideal bodily substance for use in measuring hydration and dehydration. Saliva is easily obtained with minimal invasiveness, but it is a complex fluid. Approximately 99% of saliva is water, and the remaining 1% comprises large organic molecules (such as proteins), small organic molecules (such as urea), and electrolytes (such as sodium and potassium). Whole saliva, considered as the total fluid content of the mouth, contains many other constituents, including serum components, blood cells, bacteria, bacterial products, epithelial cells, cell products, food debris and bronchial secretions. Thus, processing saliva to measure an individual's hydration level is challenging but likely highly beneficial if done effectively.

The assignee of the present application has filed previous patent applications describing systems, methods and devices for testing, measuring and analyzing saliva, to measure a subject's hydration level, as well as for measuring other substances and/or physiological parameters in a human or animal subject. These previous patent applications include U.S. patent application Ser. No. 16/197,530 (U.S. Pub No. 2019/0150836), titled "Saliva Testing System," filed Nov. 21, 2018; and Ser. No. 16/598,000, titled "Ion Selective Sensor," filed Oct. 10, 2019 (U.S. Pub No. 2019/0150836). The applications also include U.S. Provisional Patent Application Serial Nos.: 62/872,339, titled "Saliva Test Strip and Method," filed Jul. 10, 2019; 62/961,438, titled "Assessment of Biomarker Concentration in a Fluid," filed Jan. 15, 2020; and 62/967,694, titled "Biological Fluid Sample Assessment," filed Jan. 30, 2020. All of the above-referenced patent applications are hereby incorporated by reference into the present application, and they are referred to collectively herein as "the Incorporated Applications." The present application adds to the technologies in the Incorporated Applications by describing an improved test strip, system and method that address at least some of the objectives described above in the Background section.

In one aspect of the present disclosure, a single-use, multi-layer test strip includes electrodes, microfluidics and additional materials and structures positioned in a microfluidic channel to assist in error free sampling of saliva or other complex fluids. According to various embodiments, the test strip microfluidics are formed by layering multiple layers of materials together with an adhesive. The microfluidics have an appropriate height to draw in variably viscous fluid(s). Multiple electrodes are positioned throughout the microfluidics, to allow for electrochemical analysis of one or more analytes. In various embodiments, a material is positioned in part of the microfluidic channel to impede the flow of bubbles, debris and other interferences, without preventing flow of fluid containing biomarkers into the test strip. Multiple exit ports may be located across test strip surfaces to equalize pressure in the microfluidic channel and minimize the risk of flow or measurement errors caused by excess fluid or internal or external blockages. These features allow for reliable sampling of saliva directly from the mouth or from a collection receptacle without additional processing.

Some embodiments of the test strip also include a series of electrodes to asses sample consistency throughout the test strip microfluidics. Optionally, a test strip may include a lip, positioned at the sample entry port on the test strip, to assist in sample collection disruption of surface tension or collection of low-volume samples. Some embodiments may also include one or more one-way valves, which allow for regulation of sample flow throughout the test strip.

In another aspect of the present disclosure, a test strip for sampling a bodily fluid may include: multiple layers of a substrate material; an adhesive between at least some of the multiple layers; a microfluidic channel formed between at least some of the multiple layers; multiple electrodes on one of the multiple layers, positioned and partially exposed within the microfluidic channel; an additional material positioned at or near an entrance to the microfluidic channel, to selectively limit the flow of at least one of bubbles or debris into the microfluidic channel; and at least one exit port in at least one of the multiple layers to allow for release of pressure from the test strip. In some embodiments, the test strip is a saliva analysis test strip, and the bodily fluid is saliva.

Some embodiments of the test strip include multiple exit ports to prevent disruption of sample flow through the microfluidic channel due to blockages. For example, the exit ports may include a first exit port in a top layer of the test strip and at least a second exit port in a side of the test strip. Some embodiments include two side exit ports located in opposite sides of the test strip. In some embodiments, the entrance to the microfluidic channel serves as a sample entry port on a collection end of the test strip. Optionally, the test strip may include a lip at its collection end, to facilitate sample collection and/or sample flow.

In some embodiments, the test strip may include at least one one-way valve to regulate flow of the biological fluid through the microfluidic channel. In various embodiments, the substrate material of the multiple layers of the test strip may be, but is not limited to, paper, plastic, glass, or metal. The additional material may be a mesh material. For example, the mesh material may be nylon. In some embodiments, the multiple electrodes are screen printed on a bottom layer of the test strip. In some embodiments, the multiple electrodes are positioned throughout the microfluidic channel, and they are configured to determine whether the biological fluid is evenly distributed. In some embodiments, the multiple electrodes are configured to measure for a single analyte. Alternatively, the multiple electrodes may be configured to measure for multiple analytes. In various embodiments, the electrodes may be either functionalised electrodes or unfunctionalized electrodes.

In another aspect of the present disclosure, a method of using a saliva test strip to determine a concentration of at least one analyte in a saliva sample may involve: contacting a free end of the saliva test strip with the saliva sample to take up a portion of the saliva sample into an inlet on the free end of the saliva test strip, where the inlet leads to a microfluidic channel in the test strip; preventing bubbles from passing through the microfluidic channel by trapping the bubbles in a piece of material positioned at or near the inlet; passing the portion of the saliva sample along the microfluidic channel over multiple electrodes of the saliva test strip; and determining the concentration of the at least one analyte, using a handheld saliva analyzer into which a connection end of the saliva test strip, opposite the free end, is placed.

In some embodiments, contacting the free end involves touching the free end to the tongue or mouth of a human subject. In alternative embodiments, contacting the free end involves touching the free end to the saliva sample contained in a receptacle. The method may further involve inserting the connection end of the saliva test strip into the handheld saliva analyzer before contacting the free end with the saliva sample. Alternatively, the method may involve inserting the connection end of the saliva test strip into the handheld saliva analyzer after contacting the free end with the saliva sample. In some embodiments, the piece of material positioned at or near the inlet comprises a polymer mesh material.

These and other aspects and embodiments are described in greater detail below, in relation to the attached drawing figures.

DETAILED DESCRIPTION

The present application describes various embodiments and features of a biological fluid analysis test strip, system and method. Although the following disclosure focuses on the use of the test strips for collection and analysis of saliva, the embodiments described below, or variations of those embodiments, may be used for collection and analysis of any other bodily fluid, such as blood, sweat, urine or the like. Therefore, although embodiments are typically described below as "saliva analysis test strips" (or simply "saliva test strips"), these same strips or variations thereof may be used with other bodily fluids of a human or animal subject.

Figure 1:
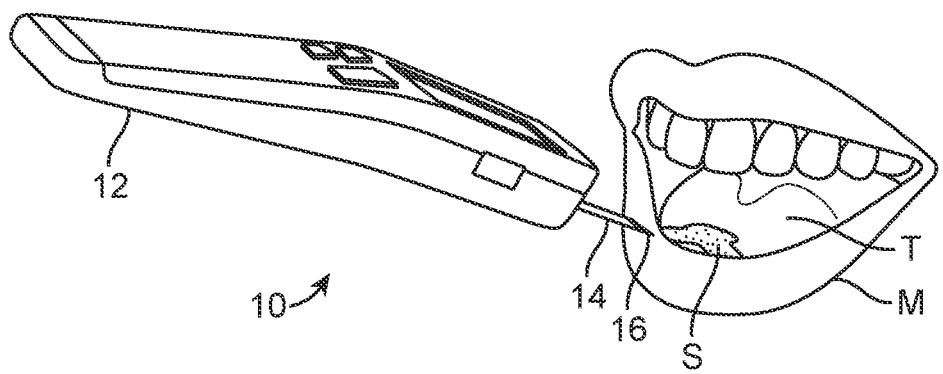
FIG. 1 is a perspective view of a saliva testing device and a human subject's mouth, illustrating a method of collecting saliva by placing the free end of the test strip of the device on the subject's tongue, according to one embodiment.

FIG. 1 is a perspective view of a subject's mouth M and a saliva analysis system 10, illustrating one method for collecting saliva S using a test strip 14. The saliva analysis system 10 includes a handheld analyzer 12 and a test strip 14 partially inserted into the handheld analyzer 12 so that a free end 16 (or "collection end") is exposed for collecting a sample of saliva S from the subject's tongue T. In this method, the free end 16 of the test strip 14 is applied directly to the subject's tongue T to collect the saliva S sample. In an alternative embodiment, the free end 16 may be placed on or in another part of the mouth M, such as the cheek. The saliva analysis system 10 may have the capability of detecting when a sufficient amount of saliva S is collected on the test strip 14. Collecting saliva by directly placing the free end 16 of the test strip 14 on the tongue T while the test strip 14 is already inserted into the handheld analyzer 12 makes the collection process simple, quick and straightforward.

Figure 2:
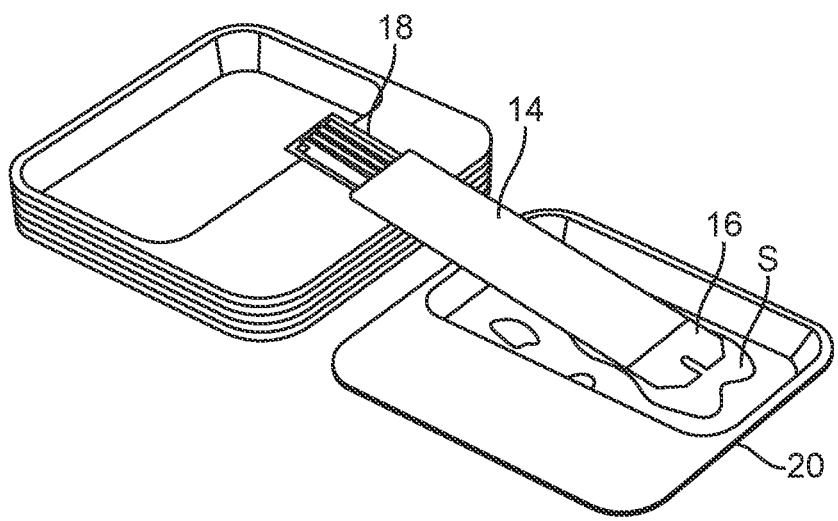
FIG. 2 is a perspective view of a saliva test strip and a saliva collection tray, illustrating a method of collecting saliva by placing the free end of the test strip in saliva that has been deposited in the collection tray, according to one embodiment.

Referring to FIG. 2, in an alternative embodiment, saliva S may first be deposited by the subject into a collection tray 20. The collection end 16 (again, synonymous with "free end") of the saliva test strip 14 may then be placed into the saliva S in the collection tray 20. Here, the test strip 14 is shown by itself, and collection may be done that way. Alternatively, the saliva S may be collected from the collection tray 20 with the test strip 14 inserted into the handheld analyzer 12.

Figure 3:
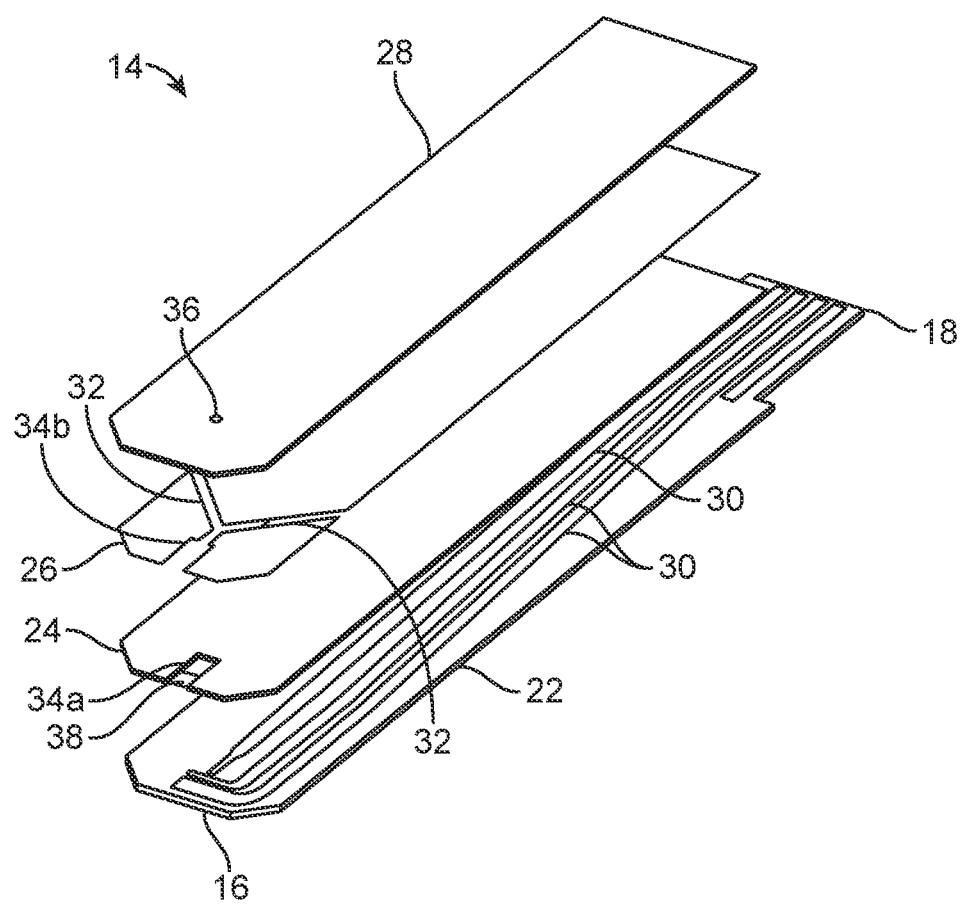
FIG. 3 is an exploded view of a test strip with mesh and multiple exit pores, according to one embodiment.
Figure 4:
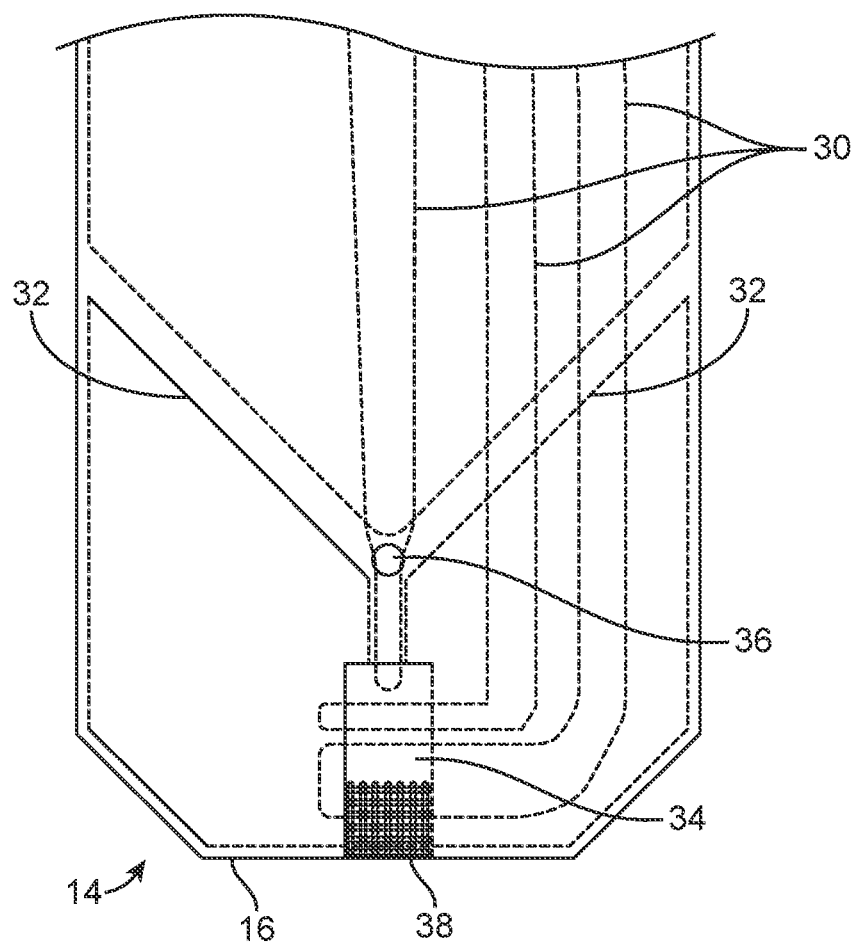
FIG. 4 is a top, partially transparent view of the free (or "collection") end of the test strip of FIG. 3.

Referring to FIGS. 3 and 4, a saliva analysis test strip 14 as described herein typically includes multiple layers 22, 24, 26, 28 of material sandwiched together. FIG. 3 shows an exploded view of the saliva test strip 14 (in this embodiment including four layers 22, 24, 26, 28), and FIG. 4 shows a top, partially transparent view of a distal portion of the test strip 14 at the free end 16. Any suitable materials may be used to form the layers 22, 24, 26, 28, such as but not limited to paper, plastic, glass, and metal. The layers 22, 24, 26, 28 may be attached to one another via one or more pieces of adhesive, such as but not limited to double-sided tape. In some embodiments, the adhesive may be screen printed. One or more microfluidic channels 34 (including 34a and 34b) in the test strip 14 are formed by sandwiching the layers 22, 24, 26, 28 together. The height of the microfluidic channel(s) 34 may be configured to allow for rapid sample flow of fluids of variable viscosity. The free end 16 of the saliva test strip 14 is configured to be placed in a sample of saliva and to take an amount of the saliva into the inlet of the microfluidic channel 34. The back end 18 (or "insertion end") of the test strip 14 is inserted into the handheld saliva analyzer 12 and connects with internal electronics of the analyzer 12 to allow saliva (or other fluid in other embodiments) to be travel to the handheld analyzer 12 and be analyzed. In the illustrated embodiments, the electrodes 30 extend to the back end 18 of the test strip 14.

In the embodiment of FIGS. 3 and 4, electrodes 30 are screen printed on the bottom layer 22 (or "first layer") of material, to allow for electro-chemical analysis. A second layer 24 of material includes a cutout forming a microfluidic channel 34a, and a mesh material 38 disposed over part of the microfluidic channel 34a. A third layer 26 of material includes a second layer of the microfluidic channel 34b and two exit channels 32. The microfluidic channel 34 is formed by the combination of channel 34a and channel 34b, and as a whole the microfluidic channel is structured to draw fluid across the electrodes 30, which are positioned to allow for detection of fluid fill, assessment of fluid consistency throughout the microfluidic channel(s) 34, and electro-chemical measurement of the sample. In an alternative embodiment, multiple sample chambers may be formed, to allow for chemical analysis of multiple analytes. A one-way valve may also optionally be included, to prevent backflow of chemicals between sample chambers. The two exit channels 32 allow for pressure venting from the saliva test strip 14, as will be described further below. The fourth or top layer 28 of material (also called the "cover") includes a sample exit port 36, which works with the two exit channels 32 to release pressure from the test strip 14. FIG. 4 shows the microfluidic channel 34, mesh material 38, electrodes 30, exit channels 32 and sample exit port 36 in top view.

When collecting viscous fluids, such as saliva, voids can form and/or debris and/or bubbles in the samples can enter the sampling chambers, affecting both the total volume of available fluid and measurement accuracy and consistency. To account for these issues, some test strip embodiments may include measurement electrodes throughout the sample chamber. In some embodiments, multiple measurements are made for the same analyte through the sample chamber. Consistency between measurements is used to confirm that the sample is uniformly distributed through the test strip microfluidics. In another embodiment, an average of the measurements of the analyte is calculated. In another embodiment, multiple measurements are made, and any inconsistent or outlier measurements are discarded before the measurements are sent to a mathematical algorithm to calculate the properties of the measured analyte.

As discussed above, bubbles and/or debris in microfluidic channel(s) 34 of a test strip 14 can adversely affect measurement accuracy. To avoid this, saliva is typically processed though centrifugation or a filter prior to measurement. However, this added process makes analyzing saliva more complex and can potentially filter out analytes that the user wishes to analyze. To combat this challenge, the test strip 14 illustrated in FIGS. 3 and 4 includes a mesh material 38 (e.g., polymer mesh, nylon mesh) strategically located in the second layer 24 within the microfluidic channel 34*a* to block the flow of debris and bubbles into the microfluidic channel 34*a*, without preventing flow of the saliva sample. This removes the need for sample processing to remove debris and bubbles prior to measurement, ensuring a uniform fluid layer is formed throughout the microfluidic channel 34*a*. The mesh material 38 traps debris, and a thin microfluidic channel 34*b* (void in the third layer 26) above the mesh material 38 allows the bodily fluid sample to flow.

Generally, the mesh material 38 (or other material in alternative embodiments, such as paper or plastic) provides a high energy surface at the entrance of the test strip 14, to filter/trap bubbles. In some embodiments, the mesh material 38 is positioned specifically at the entrance of the microfluidic channel 34. The height of the mesh material 38 may be chosen so that when it is placed inside the microfluidic channel 34 of the test strip, the effective height of the void in the microfluidic channel 34 where fluid can flow is controlled, for example less than 50 micrometers. Essentially, the mesh material 38 creates a thinner microfluidic channel 34 and affects the pressure that the sample and air bubbles experience in the microfluidic channel 34. The height of the microfluidic channel 34 is configured to be sufficiently short to impede the flow of bubbles and also sufficiently high to permit flow to allow the test strip 14 to fill in a timely manner. In alternative embodiments, rather than using mesh material 38, a high energy surface may be provided by depositing materials with bead-like structures. In other embodiments, a high energy surface can be formed by printing or depositing other materials at the test strip 14 entrance.

Figure 5:
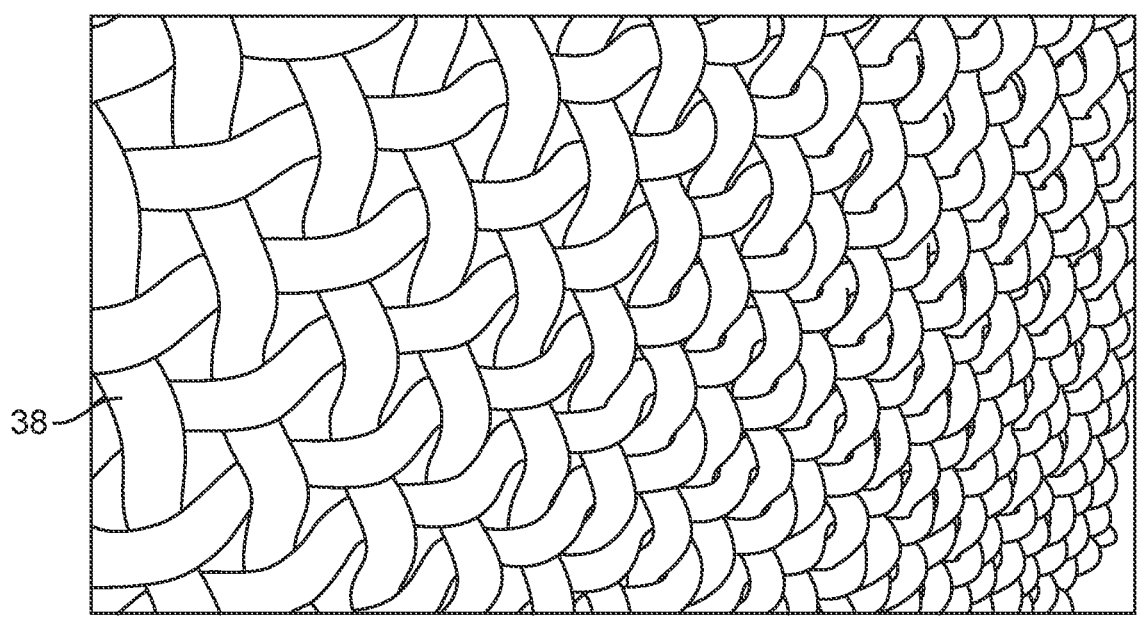
FIG. 5 is a perspective view of a threaded mesh material of the type used in embodiments of the test strips described herein, where the mesh material is used to create a high energy surface to capture bubbles in saliva.

FIG. 5 is a magnified view of a piece of threaded mesh material 38 that may be used in a saliva test strip 14.

Figures 6, 7, 8:
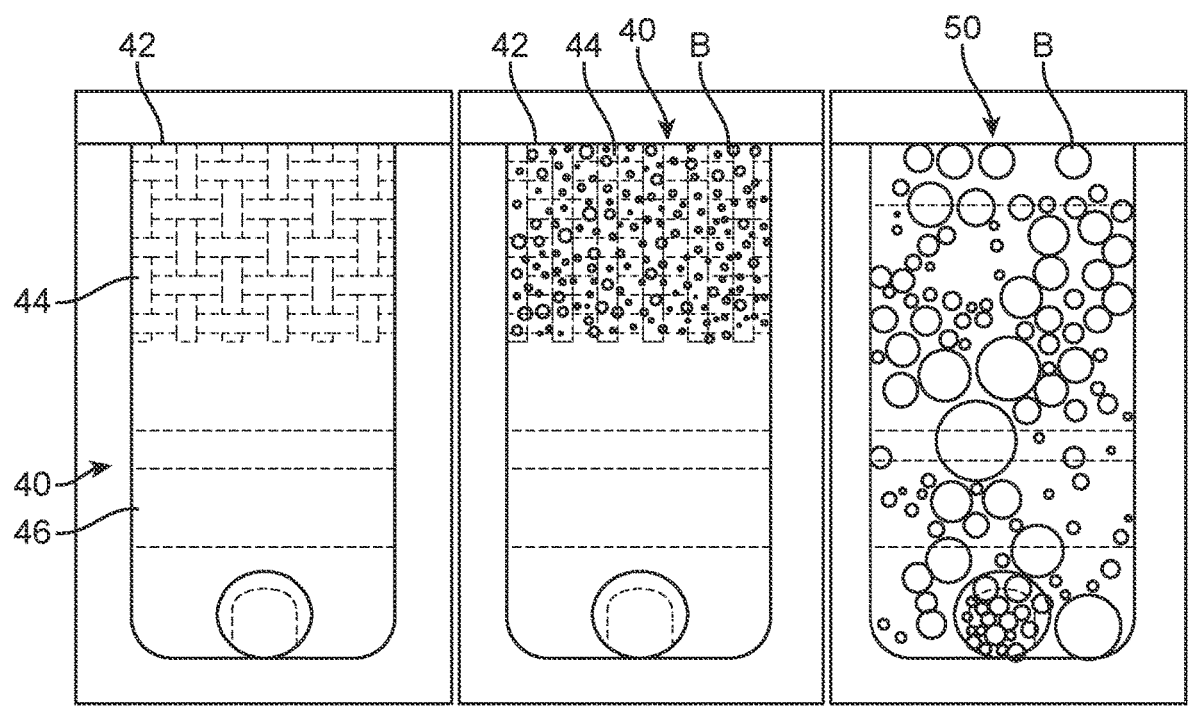
FIG. 6 is a top view of a portion of a test strip including a mesh material, according to one embodiment.
FIG. 7 is a top view of the portion of the test strip of FIG. 6, showing bubble trapping at the top of the image, where the mesh material is located.
FIG. 8 is a top view of a prior art test strip with no mesh material, showing how bubbles distribute throughout the strip.

FIG. 6 is a top view of a distal portion of a saliva analysis test strip 40 (or "saliva test strip") with a piece of mesh material 44 placed across the opening 42 of the microfluidic channel. The dark portions of the test strip 40 are electrodes 46. The height, material and thread-count of the mesh material 44 are configured to maximize flow time and bubble/debris blocking. In experiments, the mesh material 44 has been shown to greatly improve the consistency between saliva sample measurements.

FIG. 7 shows the saliva test strip 40 of FIG. 6, after a saliva sample has been deposited in the opening 42 of the microfluidic channel. Bubbles B from the sample are trapped in the mesh material 44 and prevented from traveling beyond the mesh material 44 and down the length of the saliva test strip 40. In an alternative embodiment, the mesh material 44 may be placed in a different location in the microfluidic channel, for example not right at the opening 42.

FIG. 8 is a top view of a prior art saliva test strip 50, with saliva deposited on it. In contrast the embodiment of FIGS. 6 and 7, the prior art test strip 50 allows bubbles B to spread/travel throughout the strip 50, which confounds the measurement process.

Figure 9:
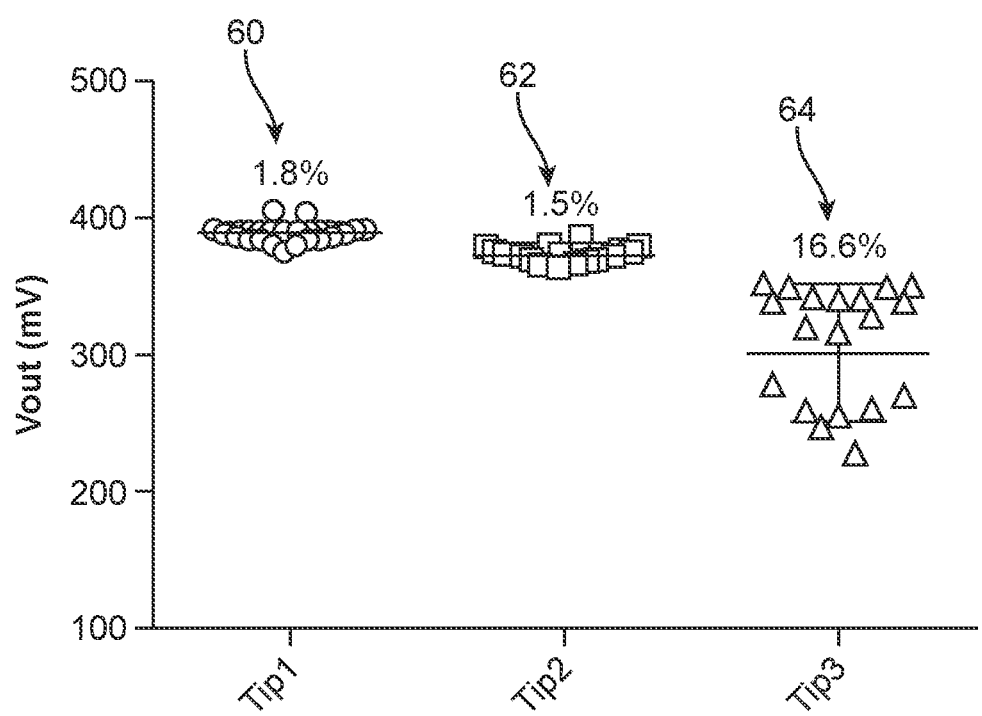
FIG. 9 is a chart, illustrating test results related to variations in measurements from several different embodiments of saliva test strips, according to various embodiments.

FIG. 9 is a chart, showing experimental results of saliva measurement using three different types of saliva test strips. Results for Tip1 60 and Tip2 62 are from two saliva test strips with mesh material positioned at the entrance of the microfluidic channel of each strip. The percentages of the results 60, 62 (1.8% and 1.5%±0.3%) represent the amount of variation in saliva measurements found when multiple measurements were taken of the same saliva sample using multiple saliva test strips having Tip1 and Tip2. By contrast, the results measured with a saliva test strip having Tip3 64 are derived from testing with a prior art test strip, such as the one shown in FIG. 8, which has no mesh material. Using the prior art test strip with Tip3, the results 64 showed a 16.6%±0.3% variation in the determined analyte concentration between multiple saliva test strips.

Figure 10:
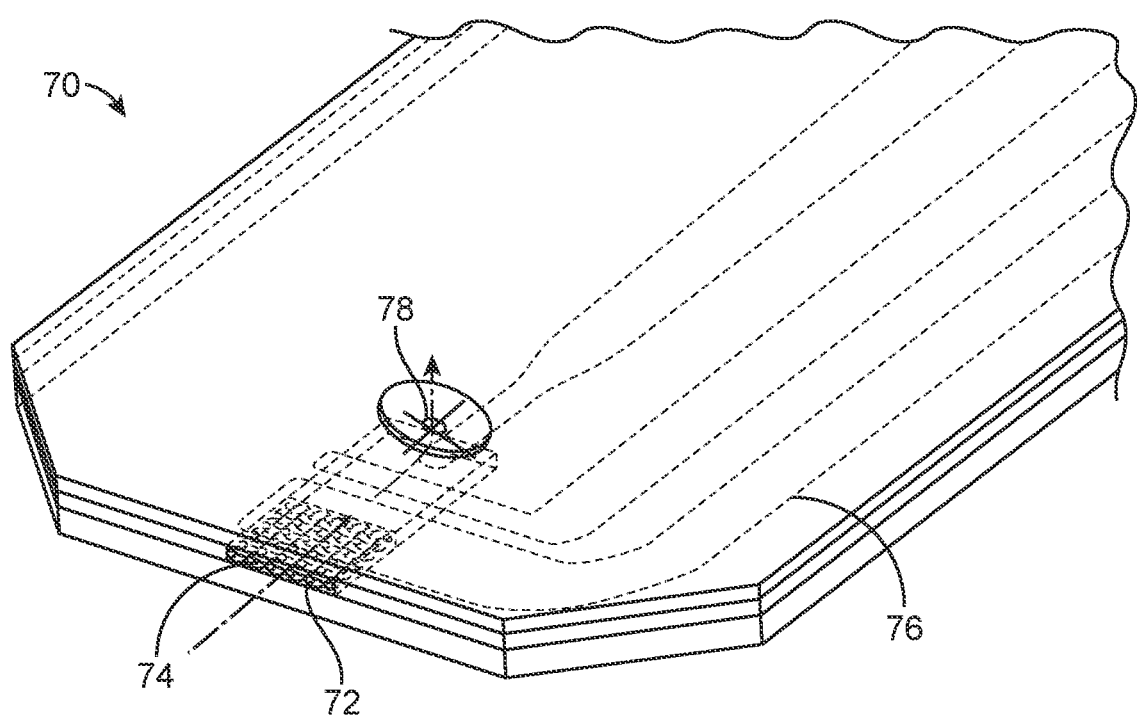
FIG. 10 is a perspective view of a distal portion of a test strip with one exit port on a top surface, according to one embodiment.

Referring to FIG. 10, a distal portion (free end/collection end) of one embodiment of a saliva analysis test strip 70 is shown in perspective view. In this embodiment, the saliva test strip 70 includes a microfluidic channel having an inlet 72, a piece of mesh material 74 located in the channel at the inlet 72, and a microfluidic channel exit port 78 located in the cover layer 76 to equalize pressure. In some embodiments, like this one, the saliva test strip 70 includes only one microfluidic channel exit port 78. In some cases, when collecting saliva or other viscous and complex fluids, this exit port 78 can become covered by the analyte or otherwise blocked, resulting in a disruption of sample collection. Stringent collection methodology may be advisable with such embodiments, to avoid blockage of the exit port 78. This may be difficult, especially when collecting saliva directly from a mouth (particularly when self-testing), since it is often difficult to see the small sampling site on the free end of the test strip 70.

Figure 11:
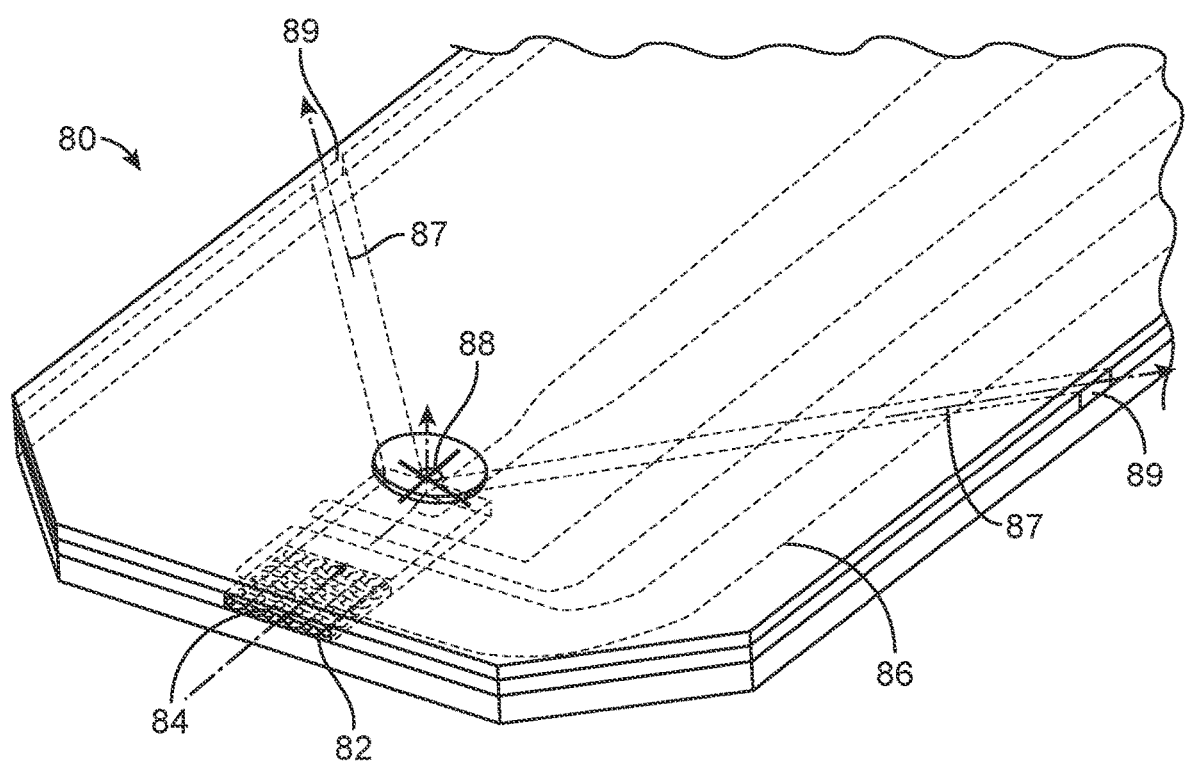
FIG. 11 is a perspective view of a distal end of a test strip with multiple exit ports, according to one embodiment.

Referring to FIG. 11, in an alternative embodiment, to minimize the complications arising from blocking a single exit port, a saliva test strip 80 may include multiple microfluidic channel exit ports 88, 89. (The exit ports 88, 89 in this embodiment are similar to those of the saliva test strip 14 pictured in FIGS. 3 and 4.) In the illustrated embodiment, the saliva test strip 80 includes a microfluidic channel having an inlet 82, a piece of mesh material 84 located in the channel at the inlet 82, and a microfluidic channel exit port 88 located in the cover layer 86 to equalize pressure. Additionally, the saliva test strip 80 includes two microfluidic exit channels 87 ending in two microfluidic channel side exit ports 89. Thus, the saliva test strip 80 includes a total of three microfluidic channel exit ports 88, 89. Therefore, if any single exit port 88, 89 is blocked by poor sample collection technique, the flow of fluid in the microfluidic channel will not be disrupted. The microfluidic channel exit ports 88,89 are located distantly from each other, to reduce the likelihood of all three being blocked by poor sample collection technique. If any single port 88, 89 remains unblocked, a successful sample collection can still occur.

Figure 12A:
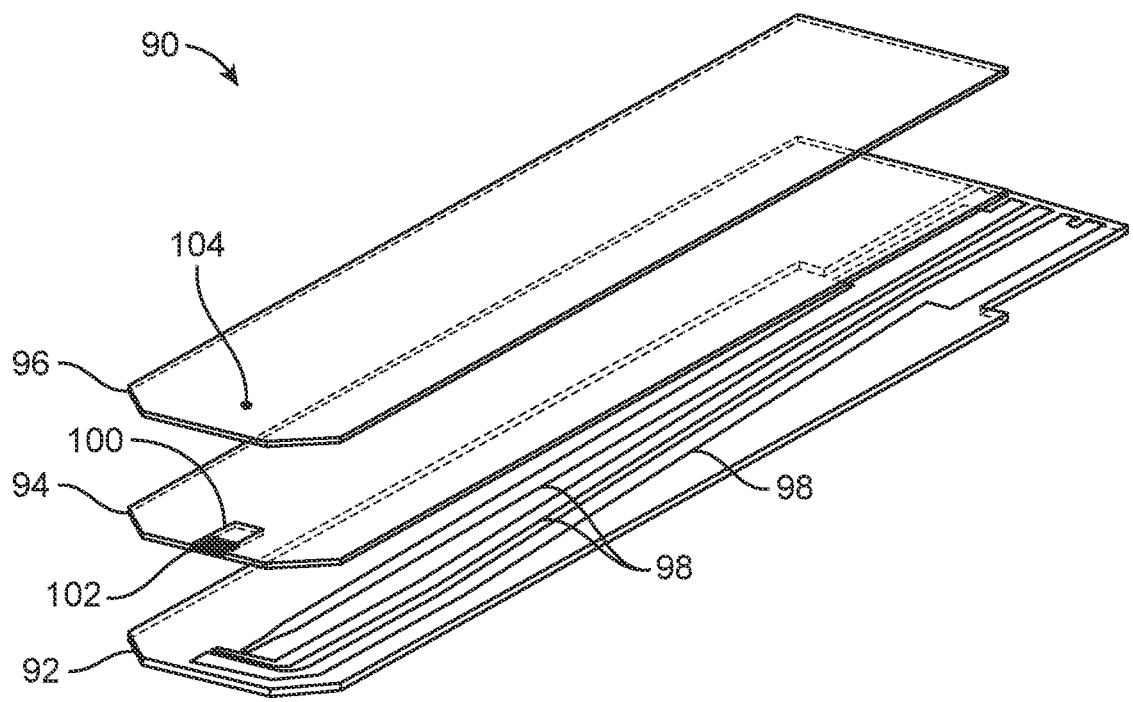
FIGS. 12A and 12B are exploded and perspective views, respectively, of a saliva analysis test strip, according to an alternative embodiment.
Figure 12B:
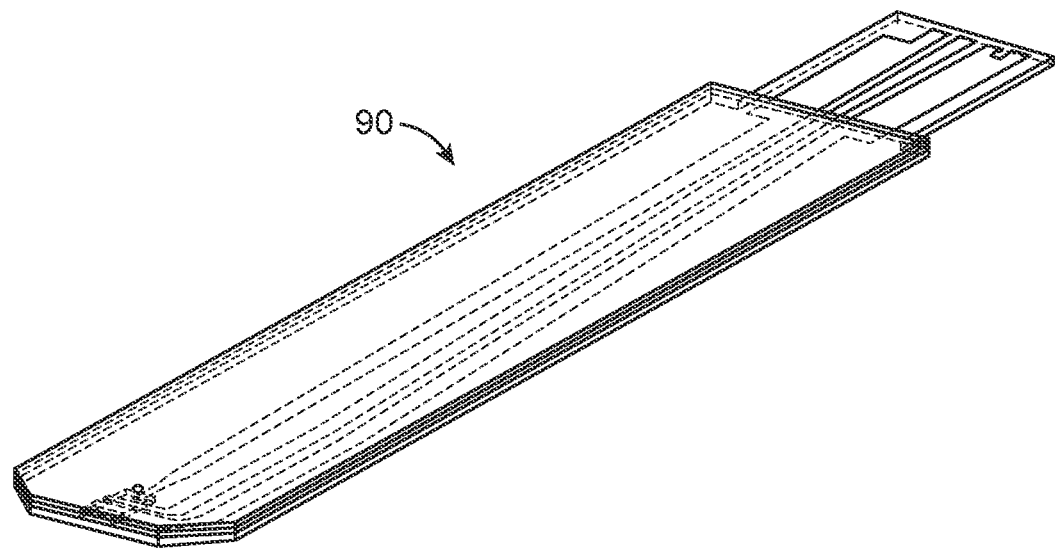

FIGS. 12A and 12B are exploded and perspective views, respectively, of a saliva analysis test strip 90 according to another alternative embodiment. In this embodiment, the saliva test strip 90 includes a bottom layer 92 (or "first layer"), a middle layer 94 (or "second layer"), and a top layer 96 (or "third layer" or "cover"). The bottom layer 92 includes multiple electrodes 98, the middle layer 94 includes a microfluidic channel 100 with a piece of mesh material 102 located at its inlet, and the top layer 96 includes one exit port 104. Unlike the embodiment described above, this embodiment of the saliva analysis test strip 90 includes only three layers 92, 94, 96 and only one exit port 104.

Figure 13:
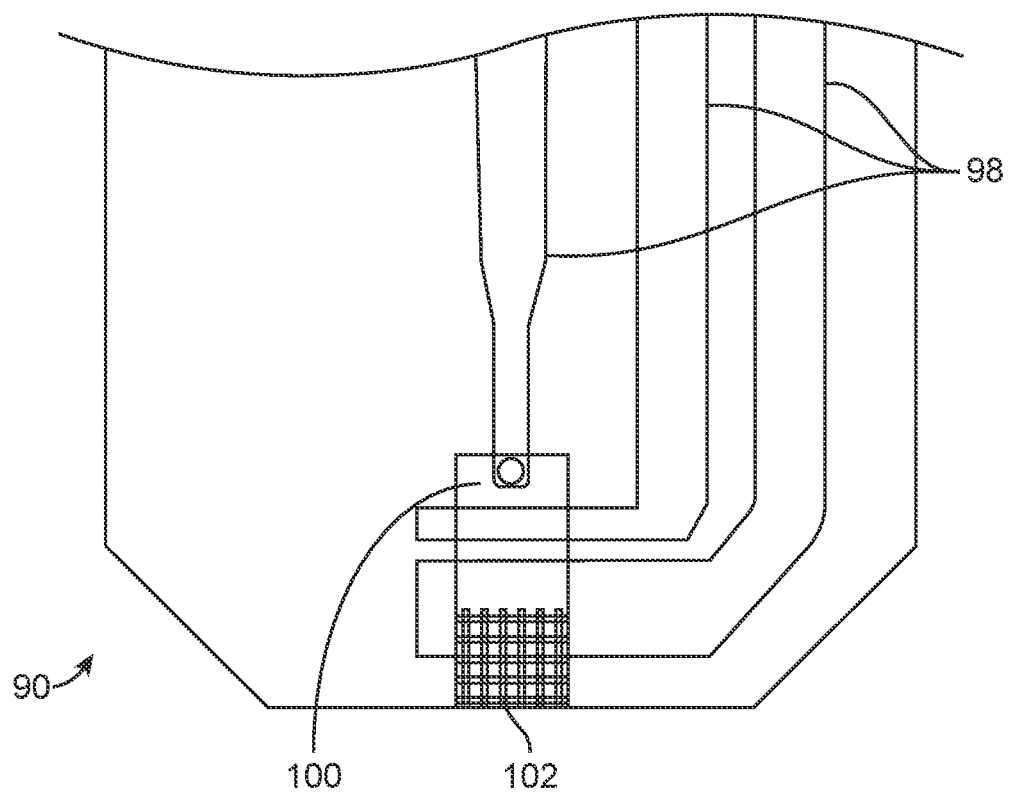
FIG. 13 is a top view of the free end of the saliva analysis test strip of FIGS. 12A and 12B.
Figure 14:
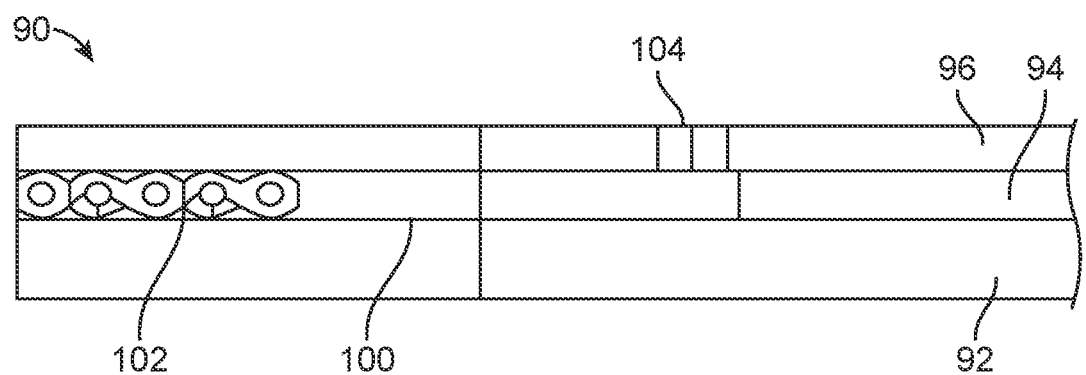
FIG. 14 is a side view of the free end of the saliva analysis test strip of FIGS. 12A and 12B.
Figure 15:
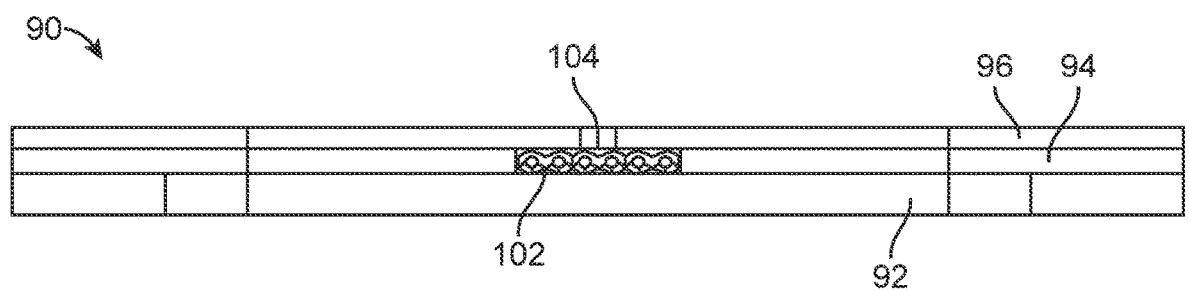
FIG. 15 is a front view of the free end of the saliva analysis test strip of FIGS. 12A and 12B.
Figure 16:
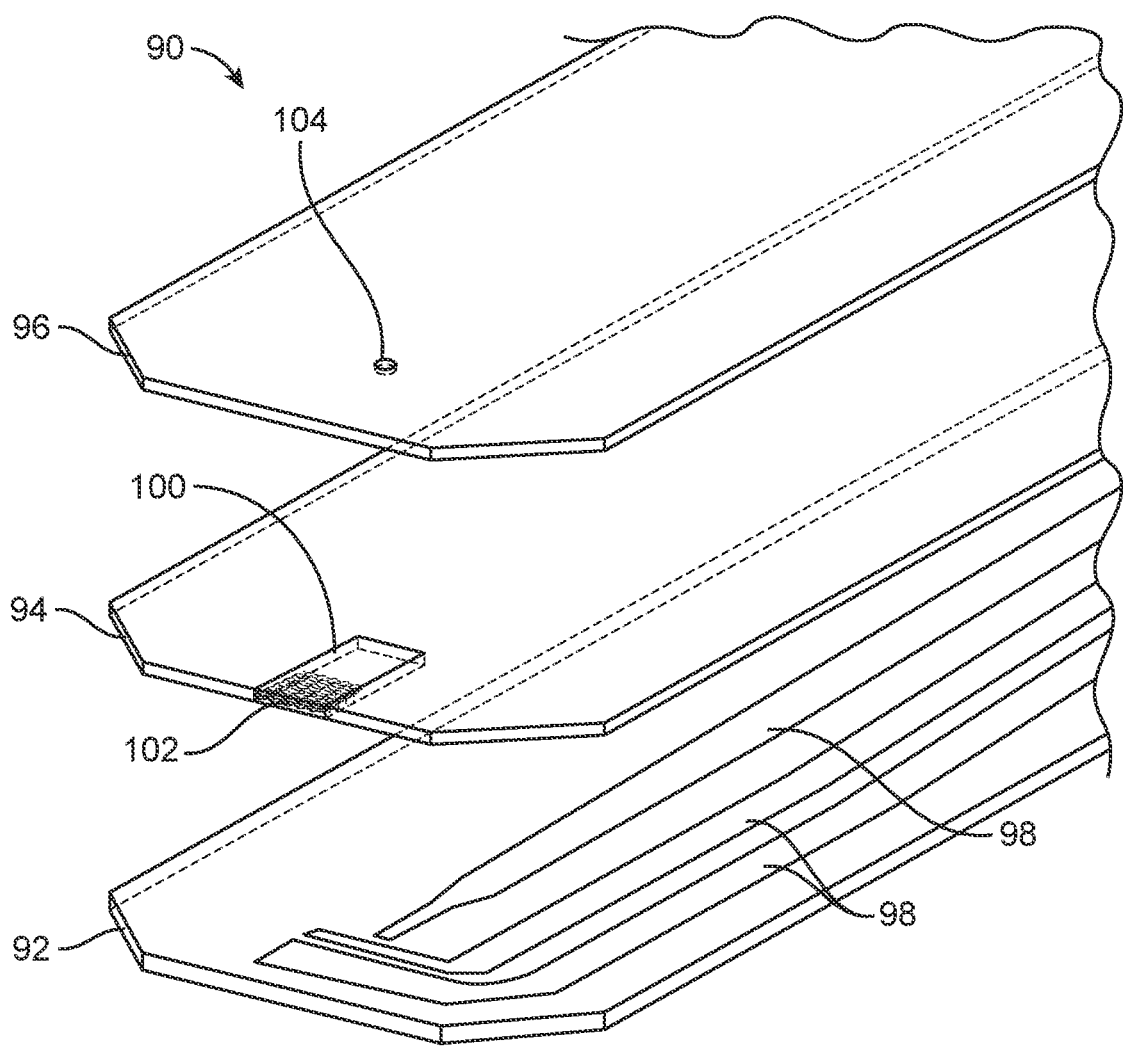
FIG. 16 is a magnified, exploded view of the free end of the saliva analysis test strip of FIGS. 12A and 12B.

FIG. 13 is a close-up, top view of a distal portion of the saliva test strip 90 of FIGS. 12A and 12B. FIG. 14 is a side view of a distal portion of the saliva test strip 90. FIG. 15 is a front view of the distal/free/collection end of the saliva test strip 90. FIG. 16 is an exploded, close-up view of a distal portion of the saliva test strip 90.

Figure 17:
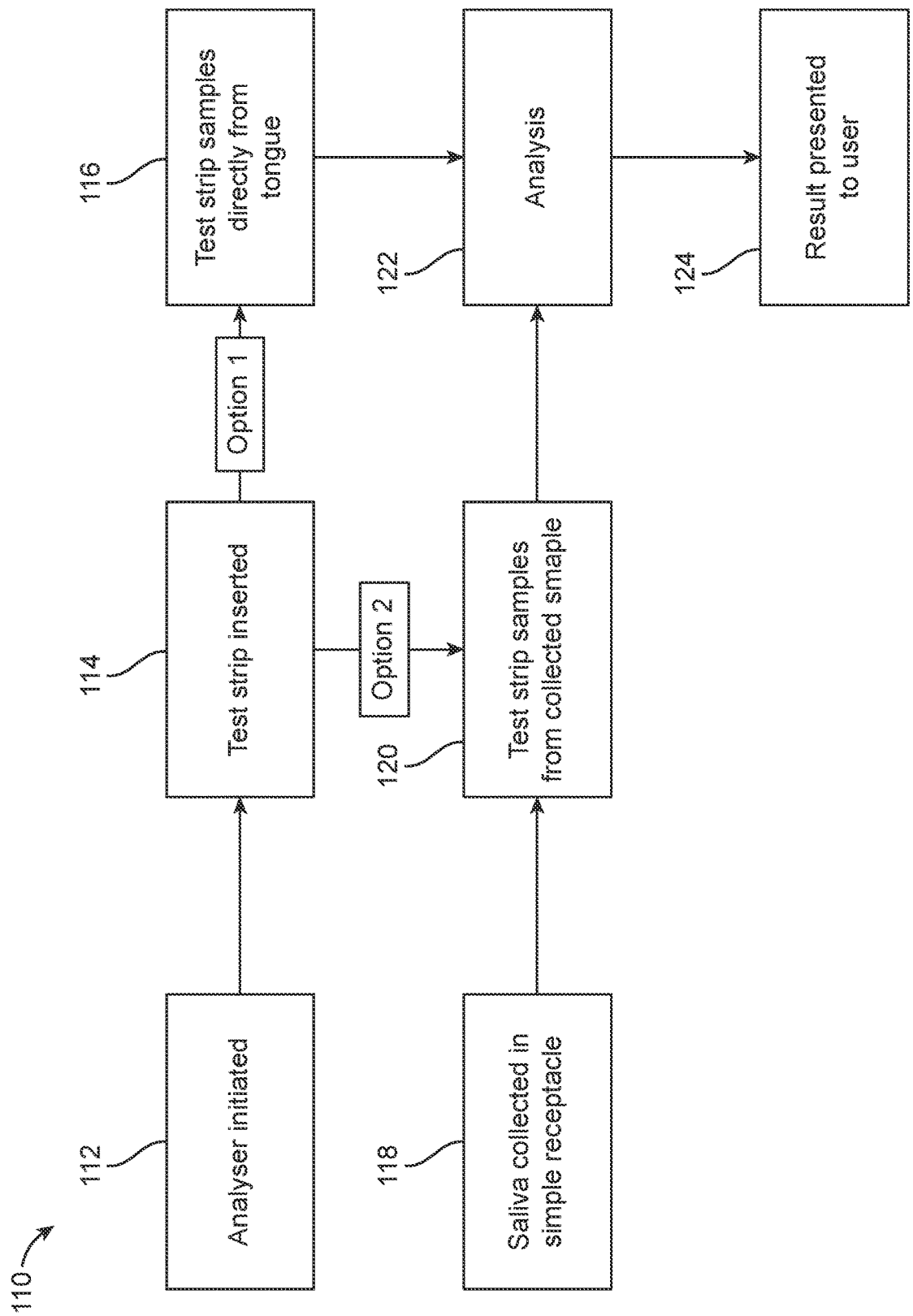
FIG. 17 is a flow diagram illustrating a method for sampling saliva directly from a subject's tongue onto a test strip, according to one embodiment.

FIG. 17 is a flow chart that illustrates a method 110 for direct-from-mouth, processing-free sampling and analysis of saliva, using the test strips described herein. By eliminating (or in other embodiments at least reducing) sample processing requirements prior to saliva analysis, the method 110 makes it easy to measure and use saliva biomarkers for tracking of health and fitness. The features of the saliva test strips described above allow for reliable, direct-from-mouth sampling of saliva for the electrochemical measurement of biomarkers. In this method 110, the user first initiates the handheld saliva analyzer 12. Next, the test strip is inserted 114 into the handheld analyzer 12 (or other point-of-care analysis system in some embodiments). Implementing Option 1, the free end of the test strip is then used to sample saliva directly from the user's tongue 116. This may be accomplished by directly applying (or "tapping") the free end against the tongue (e.g., as illustrated in FIG. 1), to collect a saliva sample, which is then analyzed 122 by the handheld analyzer 12. In cases where direct sampling is not possible or desirable, a saliva sample may be collected in a simple receptacle 118 (e.g., as illustrated in FIG. 2). Following Option 2 of the method 110, the free end of the test strip may then be inserted into the saliva sample in the receptacle 120, and the saliva sample may then be analyzed 120 in the same way it would be if collected directly from the mouth, without processing the saliva before analyzing. Finally, at the end of either option of the method 110, saliva measurement results are provided to the user 124.

Although the above description is believed to be complete and accurate, various changes to any of the embodiments and features described herein may be made, without departing from the scope of the invention. For example, features described in relation to one embodiment of a saliva analysis test strip may be applied to a different embodiment. As another example, method steps may be eliminated and/or the order of steps may be altered, without departing from the scope of the invention.

We claim:

1. A test strip for sampling a bodily fluid, the test strip comprising:
   multiple layers of a substrate material;
   an adhesive between at least some of the multiple layers;
   a microfluidic channel formed between at least some of the multiple layers;
   multiple electrodes on one of the multiple layers, positioned and partially exposed within the microfluidic channel;
   an additional material positioned at or near an entrance to the microfluidic channel, to selectively limit the flow of at least one of bubbles or debris into the microfluidic channel; and
   multiple exit ports in at least one of the multiple layers to allow for release of pressure from the test strip and to prevent disruption of sample flow through the microfluidic channel due to blockages, wherein the multiple exit ports comprise:
   a first exit port in a top layer of the multiple layers; and
   at least one second exit port in a side edge of the test strip.

2. The test strip of claim 1, wherein the test strip comprises a saliva analysis test strip, and wherein the bodily fluid comprises saliva.

3. The test strip of claim 1, wherein the at least one second exit port comprises two side exit ports located in opposite side edges of the test strip.

4. The test strip of claim 1, wherein the entrance to the microfluidic channel comprises a sample entry port on a collection end of the test strip.

5. The test strip of claim 4, further comprising a lip at the collection end of the test strip, configured to facilitate at least one of sample collection or sample flow.

6. The test strip of claim 1, further comprising at least one one-way valve configured to regulate flow of the biological fluid through the microfluidic channel.

7. The test strip of claim 1, wherein the substrate material of the multiple layers is selected from the group consisting of paper, plastic, glass, and metal.

8. The test strip of claim 1, wherein the additional material comprises a mesh material.

9. The test strip of claim 8, wherein the mesh material comprises nylon.

10. The test strip of claim 1, wherein the multiple electrodes comprise screen printed electrodes positioned on a bottom layer of the multiple layers.

11. The test strip of claim 1, wherein the multiple electrodes are positioned throughout the microfluidic channel, and wherein the multiple electrodes are configured to determine whether the biological fluid is evenly distributed.

12. The test strip of claim 1, wherein the multiple electrodes are configured to measure for a single analyte.

13. The test strip of claim 1, wherein the multiple electrodes are configured to measure for multiple analytes.

14. The test strip of claim 1, wherein the multiple electrodes are selected from the group consisting functionalised electrodes and unfunctionalized electrodes.

15. A method of using a saliva test strip to determine a concentration of at least one analyte in a saliva sample, the method comprising:
   providing the saliva test strip comprising:
      multiple layers of a substrate material;
      an adhesive between at least some of the multiple layers;
      a microfluidic channel formed between at least some of the multiple layers;
      multiple electrodes on one of the multiple layers, positioned and partially exposed within the microfluidic channel;
      an additional material positioned at or near an entrance to the microfluidic channel, to selectively limit the flow of at least one of bubbles or debris into the microfluidic channel; and
      multiple exit ports in at least one of the multiple layers to allow for release of pressure from the test strip and to prevent disruption of sample flow through the microfluidic chamiel due to blockages, wherein the multiple exit ports comprise:
         a first exit port in a top layer of the multiple layers; and
         at least one second exit port in a side edge of the test strip;
   taking up a portion of a saliva sample into an inlet on a free end of the saliva test strip by the free end of the saliva test strip contacting the saliva sample, wherein the inlet leads to the microfluidic channel in the test strip;
   preventing bubbles from passing through the microfluidic channel by trapping the bubbles in the additional material;
   passing the portion of the saliva sample along the microfluidic channel over the multiple electrodes of the saliva test strip; and
   determining the concentration of the at least one analyte, using a handheld saliva analyzer into which a connection end of the saliva test strip, opposite the free end, is placed.

16. The method of claim 15, wherein taking up the portion of the saliva sample comprises touching the free end to the tongue or mouth of a human subject.

17. The method of claim 15, wherein taking up the portion of the saliva sample comprises touching the free end to the saliva sample contained in a receptacle.

18. The method of claim 15, further comprising inserting the connection end of the saliva test strip into the handheld saliva analyzer before taking up the portion of the saliva sample.

19. The method of claim 15, further comprising inserting the connection end of the saliva test strip into the handheld saliva analyzer after taking up the portion of the saliva sample.

20. The method of claim 15, wherein the additional material comprises a polymer mesh material.

21. A test strip for sampling a bodily fluid, the test strip comprising:
- multiple layers of a substrate material;
- an adhesive between at least some of the multiple layers;
- a microfluidic channel formed between at least some of the multiple layers;
- multiple electrodes on one of the multiple layers, positioned and partially exposed within the microfluidic channel; and
- multiple exit ports in at least one of the multiple layers to allow for release of pressure from the test strip and to prevent disruption of sample flow through the microfluidic channel due to blockages, wherein the multiple exit ports comprise:
- a first exit port in a top layer of the multiple layers; and
- at least one second exit port in a side edge of the test strip.

* * * * *

UNITED STATES PATENT AND TRADEMARK OFFICE
CERTIFICATE OF CORRECTION

PATENT NO. : 11,701,036 B2
APPLICATION NO. : 16/924386
DATED : July 18, 2023
INVENTOR(S) : Thanh Cong Nguyen et al.

Page 1 of 1

It is certified that error appears in the above-identified patent and that said Letters Patent is hereby corrected as shown below:

On the Title Page

On Page 2, Column 2, Item (56) (Other Publications), Line 2: Delete "eom" and insert -- com --.

In the Specification

On Column 2, Line 18: Delete "salivation" and insert -- salivation. --.

In the Claims

On Column 10, Line 47: In Claim 15, delete "chamiel" and insert -- channel --.

Signed and Sealed this
Nineteenth Day of September, 2023

Katherine Kelly Vidal
*Director of the United States Patent and Trademark Office*